United States Patent [19]
Lehn et al.

[11] Patent Number: 5,346,996
[45] Date of Patent: Sep. 13, 1994

[54] RARE EARTH CRYPTATES, PROCESSES FOR THEIR PREPARATION, SYNTHESIS INTERMEDIATES AND APPLICATION AS FLUORESCENT TRACERS

[75] Inventors: Jean-Marie Lehn, Strasbourg; Gérard Mathis, Bagnols-sur-Ceze; Béatrice Alpha; Robert Deschenaux, both of Strasbourg; Etienne Jolu, Bagnols-sur-Ceze, all of France

[73] Assignee: Compagnie Oris Industrie, Paris Cedex, France

[21] Appl. No.: 927,063

[22] Filed: Sep. 14, 1992

Related U.S. Application Data

[60] Division of Ser. No. 737,556, Jul. 26, 1991, Pat. No. 5,162,508, which is a continuation of Ser. No. 547,316, Jul. 2, 1990, abandoned, which is a continuation of Ser. No. 147,693, Jan. 25, 1988, abandoned.

[30] Foreign Application Priority Data

Dec. 18, 1987 [FR] France ................. 87 17765

[51] Int. Cl.$^5$ ............. C07F 15/00; C07D 401/04; G01N 33/533
[52] U.S. Cl. ........................... 534/15; 435/4; 436/536; 436/546; 436/800; 530/391.5; 530/409
[58] Field of Search ............ 534/15; 436/546, 800, 436/536; 540/465, 467, 469; 530/391.5, 409; 435/4, 968

[56] References Cited

U.S. PATENT DOCUMENTS 3,888,877 6/1975 Lehn ................. 260/327

(List continued on next page.)

FOREIGN PATENT DOCUMENTS 0068875 1/1983 European Pat. Off. .

(List continued on next page.)

OTHER PUBLICATIONS

Soini et al., "Fluoroimmunoassay: Present Status and Key Problems", *Clin. Chem*, vol. 25, No. 3, 353–361, (1979).

(List continued on next page.)

*Primary Examiner*—Robert L. Stoll
*Assistant Examiner*—John M. Covert
*Attorney, Agent, or Firm*—Woodcock Washburn Kurtz MacKiewicz & Norris

[57] ABSTRACT

The invention relates to rare earth cryptates consisting of at least one rare earth salt complexed by a macropolycyclic compound corresponding to one of formulae I or II below, in which:
the ring

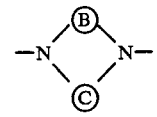

is the $N_2O_4$ macrocycle, the $N_2O_3$ macrocycle or the bis-bipyridine macrocycle;

Y is a spacer arm or group which consists of a divalent organic radical selected from linear or branched $C_1$ to $C_{20}$ alkylene groups optionally containing one or more double bonds and/or optionally being interrupted by one or more heteroatoms such as oxygen, nitrogen, sulfur or phosphorus, or from $C_5$ to $C_8$ cycloalkylene groups or $C_6$ to $C_{14}$ arylene groups, the said alkylene or arylene groups optionally being substituted by alkyl, aryl or sulfonate groups;

Z is a functional group capable of bonding covalently with a biological substance;

R is a methyl group or represents the group —Y—Z; and

R' is hydrogen or a group —COOR", in which R" is a $C_1$ to $C_{10}$ alkyl group and preferably represents the methyl, ethyl or tert.-butyl group, or alternatively R' is a group —CO—NH—Y—Z.

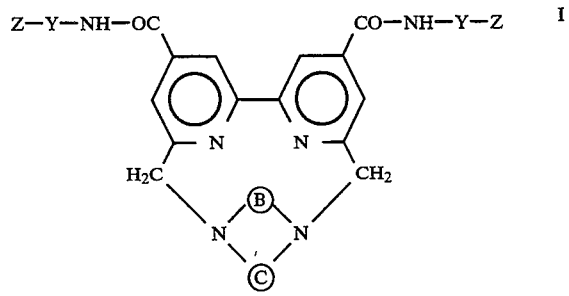

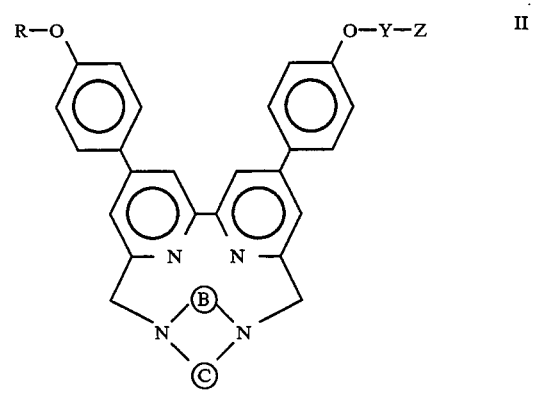

11 Claims, 2 Drawing Sheets

U.S. PATENT DOCUMENTS

| | | | |
|---|---|---|---|
| 3,966,766 | 6/1976 | Lehn | 260/327 |
| 4,058,732 | 11/1979 | Wieder | 250/461 |
| 4,156,683 | 5/1979 | Lehn | 260/338 |
| 4,256,834 | 3/1981 | Zuk et al. | 435/7 |
| 4,283,382 | 8/1981 | Frank et al. | 436/546 X |
| 4,374,120 | 2/1983 | Soini et al. | 424/7 |
| 4,631,119 | 12/1986 | Gokel et al. | 204/59 |
| 4,637,988 | 1/1987 | Hinshaw et al. | 436/546 |
| 4,761,481 | 8/1988 | Hale et al. | 436/800 X |
| 4,837,169 | 6/1989 | Toner | 436/546 |
| 4,859,606 | 8/1989 | Cram et al. | 540/469 X |
| 4,927,923 | 5/1990 | Mathis et al. | 540/456 |
| 4,994,395 | 2/1991 | Chapoteau et al. | 540/469 X |
| 5,134,232 | 7/1992 | Tsien et al. | 540/469 X |
| 5,162,525 | 11/1992 | Masilamani et al. | 540/469 X |
| 5,187,103 | 2/1993 | Czech et al. | 540/469 X |

FOREIGN PATENT DOCUMENTS

| | | |
|---|---|---|
| 0085320 | 8/1983 | European Pat. Off. . |
| 0180492A1 | 5/1986 | European Pat. Off. . |
| 0333691 | 3/1981 | Fed. Rep. of Germany . |
| 2088519 | 1/1979 | France . |

OTHER PUBLICATIONS

Newkome et al., "Synthesis and X-ray Structure of $N[CH_2)_2O)2,6-C_6H_3N_2)O(CH_2)_2]_3N$:a $D_3$ Macrobicyclic Ligand Capped By Two sp Nitrogen Atoms", *J. Am. Chem. Soc. 101,* 1047 (1979).

Dietrich et al., "Chirale Makrobicyclische Und Makrotricyclische Liganden", *Chem. 86* 443 (1974).

Kotzyba-Hibert et al., "Multisite Molecular Receptors and Co-Systems Ammonium Cryptates of Macrotricyclic Structures", *Tetrahedron Letters* vol. 21, 941–944 (1980).

Kintzinger et al., "Dymanic Properties of Molecular Complexes and Receptor-Substrate Complementarity. Molecular Dynamics of Macrotricyclic Diammonium Cryptates" *Journal of the Chemical Society, Chemical Communications* 834–836 (1981).

Lehn, "Cryptates: The Chemistry of Macropolycyclic Inclusion Complexes", *Accounts of Chemical Research,* vol. 11, No. 2 49–57 (1978).

Gansow et al., "Preparation and Characterization of Some Bifunctional Lanthanide Cryptates" *Chemical Abstracts* vol. 99, No. 10 676 (1983) Ref. 81500g.

Cuatrecasas, "Protein Purification by Affinity Chromatography", *The Journal of Biological Chemistry* vol. 245, No. 12 3059–3065 (1970).

Filipescu et al., "Substituent Effects on Intramolecular Energy Transfer II. Fluorescence Spectra of Europium & Terbium $\beta$-Diketone Chelates", *J. Phys. Chem.* 68 3324–3346 (1964).

FIG. I

RARE EARTH CRYPTATES, PROCESSES FOR THEIR PREPARATION, SYNTHESIS INTERMEDIATES AND APPLICATION AS FLUORESCENT TRACERS

This is a division of application Ser. No. 737,556, filed Jul. 26, 1991, now U.S. Pat. No. 5,162,508, which is a Rule 62 continuation of Ser. No. 547,316, as originally filed on Jul. 2, 1990, now abandoned, which is a Rule 62 continuation of Ser. No. 147,693 as originally filed on Jan. 25, 1988, now abandoned.

The present invention, which is the result of work carried out in collaboration with Professor J. M. LEHN and his research team at the University Louis Pasteur in Strasbourg, relates to the field of fluorescence and more particularly to a novel family of macropolycyclic rare earth complexes, or rare earth cryptates, which are suitable as fluorescent tracers, especially in immunoassays.

French Patent Application 84 14 799 describes macropolycyclic rare earth complexes which consist of at least one rare earth salt complexed by a macropolycyclic compound of the general formula:

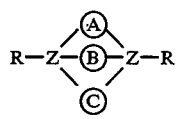

in which Z is an atom having 3 or 4 valencies, R is nothing or represents hydrogen, the hydroxyl group, an amino group or a hydrocarbon radical and the divalent radicals (A), (B) and (C) independently of one another are hydrocarbon chains which optionally contain one or more heteroatoms and are optionally interrupted by a heteromacrocycle, at least one of the radicals (A), (B) and (C) also containing at least one molecular unit or essentially consisting of a molecular unit, the said molecular unit possessing a triplet energy which is greater than that of the emission level of the complexed rare earth ion.

These cryptates are especially suitable as tracers for biological products in methods of immunological detection and determination by fluorescence.

When these rare earth cryptates are used for specifically labeling biological molecules by means of a covalent bond, they can be substituted on one or more of their constituent molecular units by one or more sufficiently accessible substituents possessing one or more molecular units permitting covalent coupling with the biological molecule under operating conditions compatible with its biological reactivity.

Among these molecular units, the following radicals may be mentioned as non-limiting examples: alkylamino, arylamino, isothiocyano, cyano, isocyano, thiocyano, carboxyl, hydroxyl, mercapto, phenol, imidazole, aldehyde, epoxide, halide, thionyl, sulfonyl, nitrobenzoyl, carbonyl, triazo, succinimido, anhydride, halogenoacetate, hydrazino, dihalogenotriazinyl, etc. (Biol. Chem. 245, 3059 (1970)). The length of the arm bonding the cryptate to the molecule of biological interest can vary from 1 to 20 atoms, for example, and can contain carbon atoms and also heteroatoms such as N, O, S and P.

Two families of rare earth cryptates carrying functional groups have now been found which can be used as fluorescent tracers for biological molecules.

The invention also relates to the processes for the preparation of these cryptates and to the synthesis intermediates.

Finally, it also relates to the application of these rare earth cryptates as fluorescent tracers for biological substances.

The rare earth cryptates carrying functional groups according to the present invention consist of at least one rare earth salt complexed by a macropolycyclic compound corresponding to one of formulae I or II below:

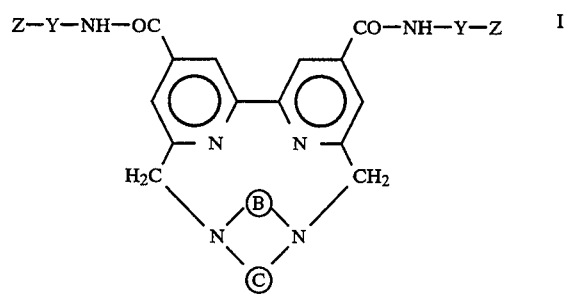

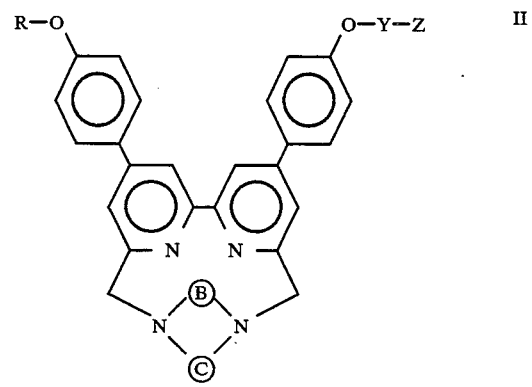

in which:
the ring of the formula

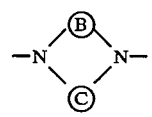

is one of the following rings:

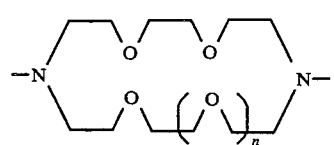

n = 0 or 1
[N₂O₄] macrocycle or (22) ring
[N₂O₃] macrocycle or (21) ring

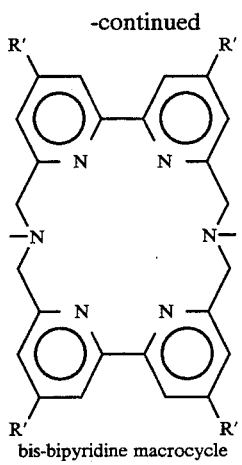

bis-bipyridine macrocycle

Y is a spacer arm or group which consists of a divalent organic radical selected from linear or branched $C_1$ to $C_{20}$ alkylene groups optionally containing one or more double bonds and/or optionally being interrupted by one or more heteroatoms such as oxygen, nitrogen, sulfur or phosphorus, or from $C_5$–$C_8$ cycloalkylene groups or $C_6$ to $C_{14}$ arylene groups, the said alkylene, cycloalkylene or arylene groups optionally being substituted by alkyl, aryl or sulfonate groups;

Z is a functional group capable of bonding covalently with a biological substance;

R is a methyl group or represents the group —Y—Z; and

R' is hydrogen or a group —COOR" in which R" is a $C_1$ to $C_{10}$ alkyl group and preferably represents the methyl, ethyl or tert.-butyl group, or alternatively R' is a group CO—NH—Y—Z.

Figure 1:
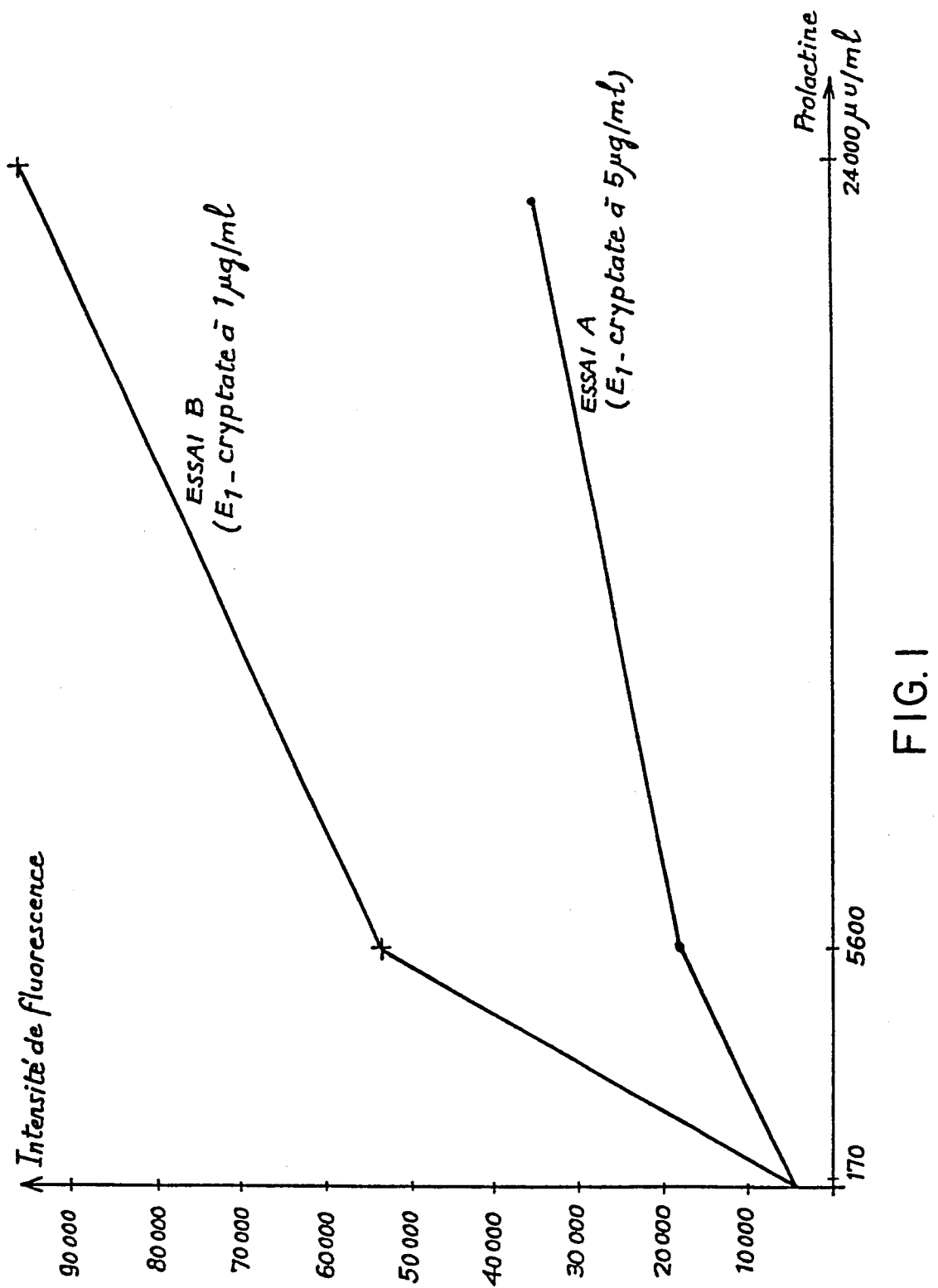
FIG. 1 is a graph plotting intensity of fluorescence exhibited by a conjugate formed from an anti-prolactin monoclonal antibody and an activated cryptate of the invention, versus amount of prolactin.

In the present description, the expression "functional group capable of bonding covalently with a biological substance" denotes any functional group capable of bonding covalently, either directly or after activation, with at least one of the groups naturally present in or artificially introduced into the said biological substance. Such groups are, in particular, the groups $NH_2$, COOH, SH or OH. Functional groups of the type mentioned above, and the activation processes, are described in detail by P. TIJSSEN in "Practice and Theory of Enzyme Immunoassays" Elsevier 1985, this document being incorporated in the present description by way of reference.

The following groups may be mentioned in particular as examples of appropriate functional groups for the purposes of the invention: amino, thio, cyano, isocyano, isothiocyano, thiocyano, carboxyl, hydroxyl, maleimido, succinimido, mercapto, phenol, imidazole, aldehyde, epoxide, halide, thionyl, sulfonyl, nitrobenzoyl, carbonyl, triazo, anhydride, halogenoacetate, hydrazino, acridine, etc.

Particular preference is given to the amino, thio and carboxyl groups, which have to be activated prior to covalent coupling with the biological substance, and to the maleimido, succinimido and isothiocyanate groups, which can bond directly with the biological substance.

In general, the cryptates according to the invention can be obtained either:

by condensation of the ring

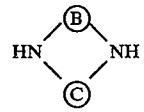

with a 6,6'-dihalogenomethyl-2,2'-bipyridine disubstituted in the 4,4'-positions, subsequent substitution by the group —NH—Y—Z or the group —Y—Z and complexation of the resulting macropolycyclic compound by a rare earth salt, or by condensation of one molecule of a 6,6'-diaminomethyl-2,2'-bipyridine disubstituted in the 4,4'-positions with two molecules of a 6,6'-dihalogenomethyl-2,2'-bipyridine disubstituted in the 4,4'-positions, subsequent substitution by the group —NH—Y—Z or the group —Y—Z and complexation of the resulting macropolycyclic compound by a rare earth salt.

It will be noted that, in the above processes, complexation by a rare earth salt can take place before the substitution step. This complexation is preferably carried out before the substitution step.

The various processes for the preparation of the cryptates according to the invention will now be described in detail.

PROCESS A

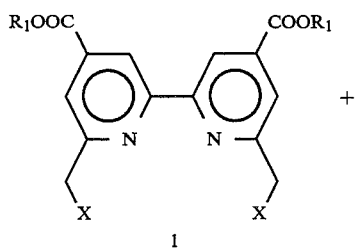

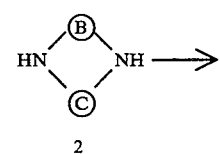

-continued

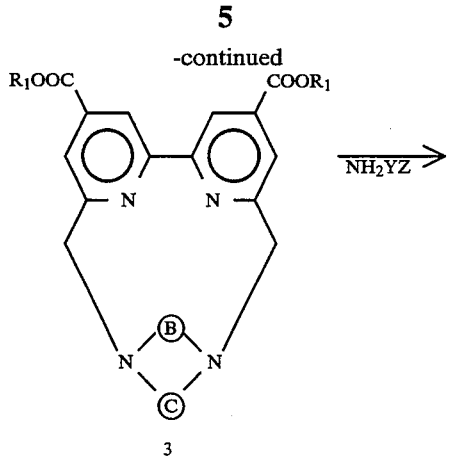

3

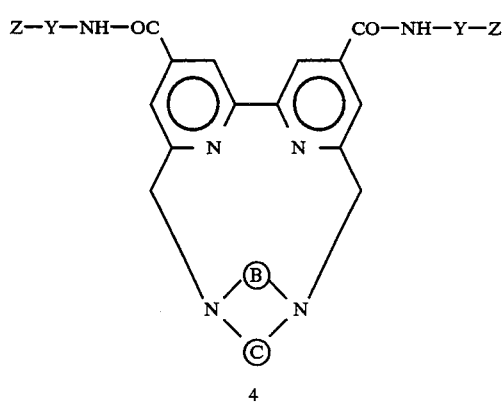

4 in which X is a halogeno group and $R_1$ is an alkyl group having from 1 to 10 carbon atoms and preferably represents the methyl, ethyl or tert.-butyl group.

In this process, the halogen derivative of bipyridine 1 is condensed with the macrocycle 2.

This reaction is advantageously carried out in an anhydrous organic solvent, for example acetonitrile, in the presence of a base such as the carbonate of an alkali metal ion, for example sodium carbonate or lithium carbonate, at the reflux temperature of the solvent. The macrobicycle 3 obtained is then in the form of a cryptate of the alkali metal ion used, for example in the form of a sodium cryptate.

The macrobicyclic compound 3 is then subjected to aminolysis by reaction with an amine of the formula $H_2N-Y-Z$, in which the groups Y and Z are as defined above, the functional group Z optionally having been blocked by conventional means. The reaction is advantageously carried out under a nitrogen atmosphere and at room temperature. When the reaction is complete, the excess amine is removed by appropriate means and the cryptate of formula 4 is recovered by conventional methods.

The compound obtained in this way is then converted to a rare earth cryptate by ion exchange, a solution of the alkali metal cryptate of the macrobicycle 4 in methanol being refluxed, if appropriate in the presence of chloroform, with a solution of a rare earth halide in methanol.

As indicated above, the alkali metal cryptate 3 can be converted to a rare earth cryptate, prior to aminolysis, by ion exchange according to the procedure described above.

The macrobicyclic compound 3 is a key intermediate for the synthesis of the cryptates of the invention. This intermediate can be in the form of an alkali metal cryptate or a rare earth cryptate. It constitutes another subject of the invention. The particularly preferred intermediates for the purposes of the invention are the compounds of formula 3 in which $R_1$ is the group $CH_3$, $C_2H_5$ or $t-C_4H_9$.

In a modified embodiment of this process, the alkali metal cryptate can be decomplexed by first being converted to the corresponding silver cryptate by reaction with an excess of silver nitrate, the said silver cryptate then being treated with $H_2S$ [Helvetica Chimica Acta, vol. 67 (1984) 2264–2269]. This gives the macropolycyclic compound 3 in the form of the free cryptand, which also constitutes a synthesis intermediate; this can subsequently be complexed by conventional means to give a rare earth cryptate.

It will be noted that the cryptates of formulae (I) or (II) in which Z is other than an amino group can be obtained from the cryptates of formulae (I) or (II) in which Z is the amino group by conventional processes well known to those skilled in the art.

PROCESS B

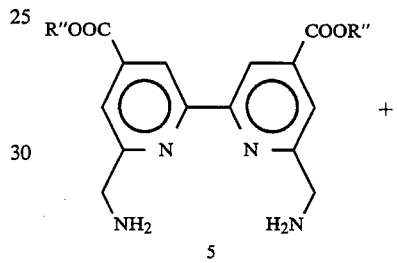

5

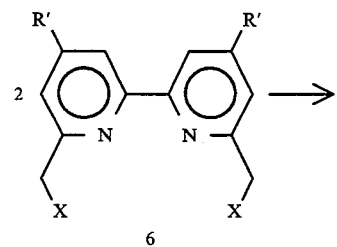

6

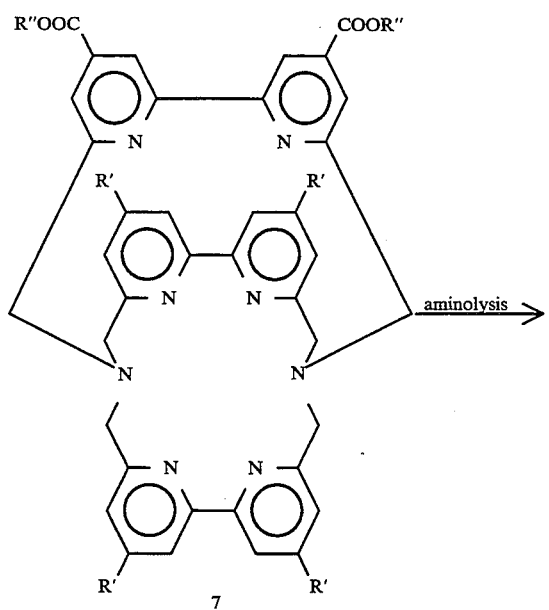

7

-continued

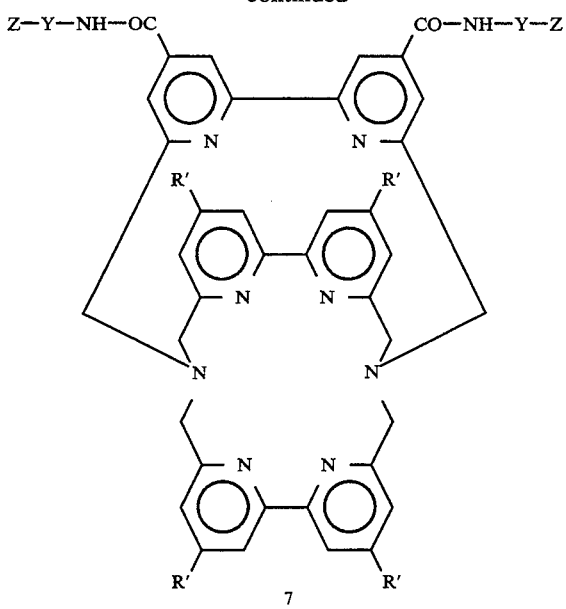

In this process, two molecules of the halogen derivative 6 are condensed with one molecule of the amine derivative 5. The condensation reaction is advantageously carried out under the same conditions as in the first step of process A, i.e. in an anhydrous organic solvent such as acetonitrile, in the presence of a base such as the carbonate of an alkali metal ion, for example sodium carbonate or lithium carbonate. The reaction is carried out at the reflux temperature of the solvent. The macropolycyclic compound 7 is obtained; this is a key intermediate for the synthesis of the cryptates according to the invention and also forms part of the framework of the invention. This macropolycyclic complex is in the form of an alkali metal cryptate, which is advantageously converted to a rare earth cryptate, prior to aminolysis, by the procedure defined above. As for process A, the alkali metal cryptate 7 can be decomplexed, in a modified embodiment, to give the corresponding macropolycyclic compound 7, or free cryptand, which is then recomplexed to give a rare earth cryptate.

The compound 7 is then subjected to aminolysis by the procedure defined above to give the macropolycyclic complex 8, i.e. a cryptate according to the invention of formula I in which

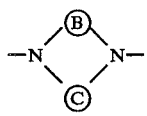

is the bis-bipyridine macrocycle and Y, Z and R' are as defined above.

The amine derivative 5 used as the starting material in process B is obtained from the halogen derivative 1 by conversion of the latter to the corresponding azido compound by reaction with NaN₃ under reflux in an organic solvent such as tetrahydrofuran, followed by reduction of the resulting azido compound in the presence of a reduction catalyst such as palladium-on-charcoal, under a hydrogen atmosphere at room temperature.

PROCESS C

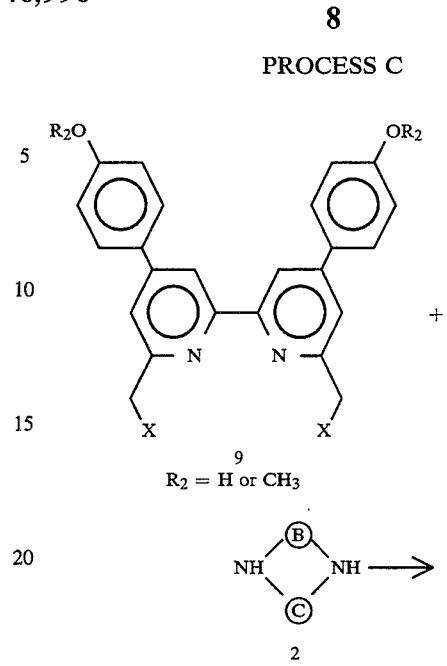

According to this procedure, the appropriately substituted halogen derivative of bipyridine 9 is first condensed with the macrocycle 2. This reaction is advantageously carried out in an anhydrous organic solvent, for example acetonitrile, in the presence of a base such as the carbonate of an alkali metal ion, for example sodium carbonate or lithium carbonate. This gives the macropolycyclic compound 10 in the form of an alkali metal cryptate. The reaction is preferably carried out at the reflux temperature of the solvent.

The macropolycyclic compound 10 is then substituted by reaction with a halide of the formula XYZ, Z and Y being as defined above and X being a halide ion.

If Z is a cyano group, it can be converted to an amino group by reduction with conventional reducing agents.

The compound 11 obtained is then converted to a rare earth cryptate by ion exchange, for example by the procedure defined above. Advantageously, a rare earth halide is dissolved in methanol and a solution of the alkali metal cryptate in methanol is added, together with a small volume of chloroform if necessary. The mixture is refluxed under an inert atmosphere and the disappearance of the alkali metal cryptate is followed by thin layer chromatography.

In a modified embodiment, the alkali metal cryptate can be decomplexed by the procedure defined above (see process A) and converted to the desired rare earth cryptate.

When the reaction is complete, the rare earth cryptate is isolated from the reaction medium by conventional processes. It is in the form of a crystalline solid.

The halogen derivative of bipyridine 9 used in the above procedure can be obtained by the process represented by the reaction scheme below:

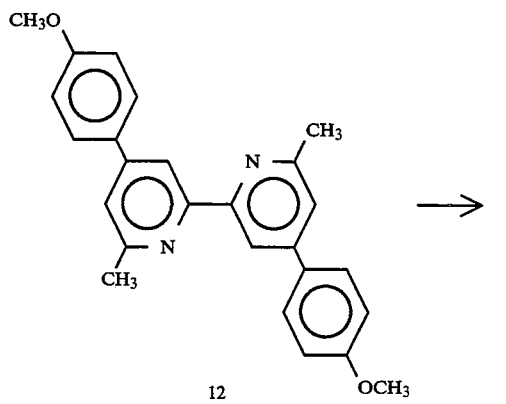

12

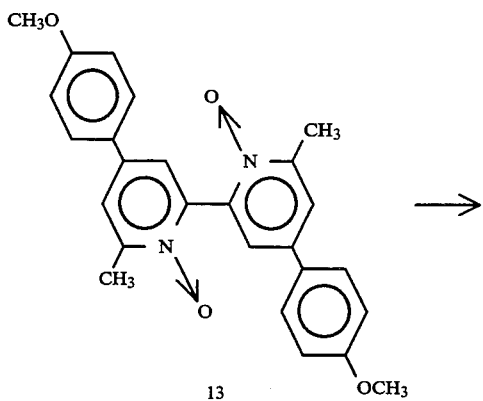

13

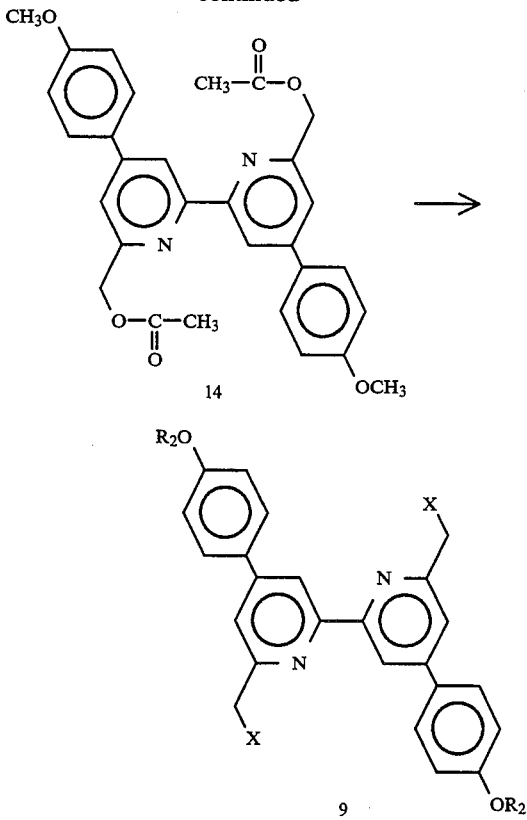

14

9

$R_2 = H$ or $CH_3$

The 6,6'-dimethyl-4,4'-di(p-methoxyphenyl)-2,2'-bipyridine of formula 12 can be obtained from 1,6-di(p-methoxyphenyl)hexa-1,5-diene-3,4-dione by the method of Kröhnke described in SYNTHESIS (1976), 1.

The compound 13 is obtained by reacting the compound 12 with m-chloroperbenzoic acid in an organic solvent such as chloroform.

The derivative 14 is then prepared by refluxing a suspension of the compound 13 in acetic anhydride.

Refluxing a solution of the compound 14 with a hydrohalic acid in acetic acid solution gives the compound 9 in which $R_2$ is H or $CH_3$, at least one of the radicals $R_2$ being hydrogen.

The compound of formula 9 is a key intermediate for the preparation of the compounds of the invention and constitutes a further subject of the invention.

The compounds according to the invention, which are stable rare earth cryptates, are soluble in water and some organic solvents such as methanol or DMSO.

The compounds of the invention are useful as fluorescent tracers for biological products and are therefore suitable as assay reagents in methods of immunological detection and determination by fluorescence, either in the so-called methods of assay by competition or in the so-called methods of assay by excess.

The invention will now be described in greater detail in the illustrative examples below.

EXAMPLE 1

Rare Earth Cryptate of [(22)(p-OCH$_3$-p-OCH$_2$CH$_2$NH$_2$-diPhbpy)]

Formula II: R=CH$_3$, Y=CH$_2$CH$_2$, Z=NH$_2$,

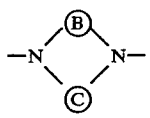

is the macrocycle (22) (process C)

A - 6,6′-Dimethyl-4,4′-di(p-methoxyphenyl)-2,2′-bipyridine (Compound 12)

A mixture of 1,6-di(p-methoxyphenyl)hexa-1,5-diene-3,4-dione (3.07 g, 9.5 mmol) prepared by the method of Kröhnke, Synthesis (1976), 1, propan-2-one-1pyridinium chloride (3.27 g, 19.1 mmol) obtained by mixing equimolar amounts of pyridine and 1-chloroacetone, and ammonium acetate (19 g) in 95.5 ml of $CH_3OH$ is refluxed for 38 h under nitrogen. After the reaction mixture has returned to room temperature, the cream-colored precipitate formed is filtered off and washed with $CH_3OH$. The crude product is used without further purification. It can be crystallized from $CH_2Cl_2$/hexane.

Yield: 70%

TLC: $R_f=0.5$ (silica, $CH_2Cl_2/CH_3OH$, 95/5)

MS: 396 (M+), 381 (M+-$CH_3$), 365 (M+-2$CH_3$), 353 (M+-$CH_3$—CO), 338 (M+-2$CH_3$—CO), 198 (M+/2).

B - 1,1′-Di(N-oxide)-6,6′-dimethyl-4,4′-di(p-methoxyphenyl)-2,2′-bipyridine (Compound 13)

A solution of m-chloroperbenzoic acid (6 g, 34.8 mmol) in 360 ml of $CHCl_3$ is added dropwise, at 0° C., to a solution of 12 (3.45 g, 8.7 mmol) in 800 ml of $CHCl_3$. The mixture is stirred overnight at room temperature. It is then washed with a saturated solution of $NaHCO_3$ until the pH is alkaline. The organic phase is separated off and concentrated. The addition of hexane causes the compound to precipitate. The precipitate is filtered off and then redissolved in a $CH_2Cl_2/CH_3OH$ mixture (90/10) and washed with a 2N solution of sodium hydroxide. The organic phase, which contains the compound 13, is separated off and the solvent is evaporated off. Furthermore, the filtrate originating from the precipitation is also washed with the 2N solution of sodium hydroxide and then concentrated and chromatographed on an alumina column with $CH_2Cl_2$ as the eluent.

Yield: 80% M.p. >250° C.

TLC: $R_f=0.5$ (alumina, $CH_2Cl_2/CH_3OH$, 95/5)

MS: 429 (MH+), 411 (M+-$H_2O$).

C - 6,6′-Diacetoxymethyl-4,4′-di(p-methoxyphenyl)-2,2′-bipyridine (Compound 14)

A suspension of 13 (1.21 g, 2.82 mmol) in 18 ml of acetic anhydride is refluxed for 1 h 30 min. The solution obtained is concentrated. 5 ml of $H_2O$ and 20 ml of $CH_2Cl_2$ are added to the pasty residue and the medium is rendered basic with a saturated aqueous solution of $NaHCO_3$. The organic phase is separated off and the aqueous phase is extracted twice with 30 ml of $CH_2Cl_2$. The resulting organic phase is dried over $Na_2SO_4$ and the solvent is evaporated off. The crude product is chromatographed on an alumina column with $CH_2Cl_2$ as the eluent:

Yield: 90% M.p.=140°-141° C.

TLC: $R_f=0.9$ (alumina, $CH_2Cl_2$ 95/5)

MS: 513 (MH+) 469 (M+-C(O)$CH_3$) 453 (M+-$CH_3COOH$) 256 (M+/2).

D - 6,6′-Dibromomethyl-4,4′-di(p-methoxyphenyl)-2,2′-bipyridine (Compound 9a: $R_2$=$CH_3$) 6,6′-Dibromomethyl-4-p-methoxyphenyl-4′-p-hydroxyphenyl-2,2′-bipyridine (compound 9b: one of the radicals $R_2$ is H, the other is $CH_3$)

A solution of 14 (0.31 g, 0.60 mmol) in 5 ml of 33% HBr/AcOH is refluxed for 12 to 13 h. 20 ml of $H_2O$ and 60 ml of $CHCl_3$ are added to the solution at room temperature. The mixture is washed with a saturated solution of $NaHCO_3$ until the washings are neutral. The organic phase is separated off and the aqueous phase is extracted with twice 20 ml of $CH_2Cl_2$. The solvent is evaporated from the resulting organic phase and the residue is chromatographed on an alumina column with $CH_2Cl_2$ and then $CH_2Cl_2/CH_3OH$ (95/5) as the eluents.

Compound 9a; $R_2$=$CH_3$ - Yield: 16%

Decomposition: 210°-215° C.

TLC: $R_f>0.9$ (alumina, $CH_2Cl_2/CH_3OH$, 95/5)

MS: 556, 555,553 (MH+), 556, 554, 552 (M+), 475, 473 (M+-Br), 394 (M+-2Br).

Compound 9b; one of the $R_2$s=H - Yield: 35%

TLC: $R_f=0.4$ (alumina, $CH_2Cl_2/CH_3OH$, 95/5)

MS: 542, 540, 538 (M+), 461, 459 (M+-Br), 380 (M+-2Br).

E - Sodium Cryptate of [(22) (p-$OCH_3$p-OH-diPhbpy)] (Compound 10)

A mixture of the macrocycle (22) (0.262 g, 1 mmol) and $Na_2CO_3$ (1.05 g, 10 mmol) in 600 ml of anhydrous $CH_3CN$ is refluxed for 30 min under nitrogen. A suspension of the compound 9b (0.54 g, 1 mmol) in 450 ml of anhydrous $CH_3CN$ is then added. The mixture is refluxed for 20 h under nitrogen. The solution obtained is filtered hot and the solvent is evaporated off. The crude product is chromatographed on alumina with $CH_2Cl_2/CH_3OH$ (95/5) as the eluent.

Yield: 60–65%

TLC: $R_f=0.6$ (alumina, $CH_2Cl_2/CH_3OH$, 90/10)

MS: 663 (M+), 640 (M+-Na) 625 (M+-Na-$CH_3$), 609 M+-Na-$OCH_3$), 595 (M+-Na-$OCH_3$-OH).

F - Sodium Cryptate of [(22) (p-$OCH_3$-p-$OCH_2CN$-diPhbpy)] (Compound 11a: Z=CN; Y=$CH_2$; R=$CH_3$)

An excess of NaH (powder) is added under nitrogen to a solution of the sodium cryptate of the compound 10 (0.042 g, 0.066 mmol) in a minimum volume of $CH_3CN$. The mixture is refluxed under nitrogen for 1 h. The solution is cooled to room temperature before the addition of bromoacetonitrile (1.2 equivalents). The mixture is stirred overnight at room temperature, under nitrogen. 20 ml of $H_2O$ and 10 ml of $CH_2Cl_2$ are added. The medium is neutralized with a saturated solution of $NaHCO_3$. The organic phase is separated off and the aqueous phase is extracted twice with 20 ml of $CH_2Cl_2$. The resulting organic phase is dried over $Na_2SO_4$ and the solvents are then evaporated off. The crude product is chromatographed on an alumina column with $CH_2Cl_2/CH_3OH$ (96/4) as the eluent.

Yield: 75%

TLC: $R_f=0.5$ (blue-violet spot), (alumina, $CH_2Cl_2/CH_3OH$, 92.5/7.5)

MS: 702 (M+), 679 (M+-Na), 663 (M+-Na-H-$CH_3$), 654 (MH+-Na-CN), 640 (MH+-Na-$CH_2CN$).

G - Sodium Cryptate of [(22) (p-$OCH_3$-p-$OCH_2CH_2NH_2$-diPhbpy)] (Compound 11b: Z=$NH_2$; Y=—$CH_2$—$CH_2$—; R=$CH_3$)

2 ml of $B_2H_6$ (1M in THF) and a further 5 ml of THF are added to a suspension of 11a (0.078 g, 0.1 mmol) in 8 ml of anhydrous THF. The mixture is stirred overnight at room temperature. 10 ml of $CH_3OH$ are added and the mixture is stirred for 20 to 30 min. The solvents are evaporated off. 20 ml of an $H_2O$/concentrated HCl mixture (1/1) are added to the residue. A yellow precipitate and the evolution of gas are observed. Dissolution takes place gradually. The solvents are evaporated off and the residue obtained is treated with an aqueous solution of NaOH (6N). The amine 11b is extracted with 25 ml of $CH_2Cl_2$. The yield is quantitative. The formation of the compound is demonstrated by $^1H$ NMR.

H - Complexation Reaction: Exchanging the Sodium with an $Ln^{3+}$ ion (Eu, Tb)

$LnCl_3.xH_2O$ (0.1 mmol) is dissolved in 25 ml of $CH_3OH$ and a solution of previously obtained sodium cryptate (0.06 mmol) in 4–8 ml of $CHCl_3$ (minimum volume) is added. The mixture is refluxed under a nitrogen atmosphere (6 hours to 4 days, depending on the sodium cryptate in question). The disappearance of the sodium cryptate is followed by TLC (alumina, $CH_2Cl_2/CH_3OH$, 90/10). When the reaction is complete, the reaction mixture is filtered, if necessary, and the solvents are evaporated off. The residue is redissolved in 15–20 ml of $CH_3OH$ and ether is added until turbidity persists (5 ml to 25–30 ml). The rare earth cryptate formed crystallizes or precipitates very rapidly or after several hours, depending on the nature of the cryptate. The formation of the cryptate is demonstrated by $^1H$ NMR and UV/visible spectroscopy.

The europium cryptate and the terbium cryptate of formula 11 were obtained by following this procedure; they have the spectroscopic characteristics given below:

Europium cryptate: UV/visible in $CH_3OH$ 280 nm maximum; 292 nm shoulder; 320 nm maximum.
Terbium cryptate: UV/visible in $H_2O$ 282 nm; 310 nm shoulder.

EXAMPLE 2

Rare Earth Cryptate of [bpy.bpy.(p-$OCH_3$-p-$OCH_2CH_2NH_2$-diPhbpy)]

$R=CH_3$; $Y=-CH_2-CH_2-$; $Z=NH_2$; $R'=H$;

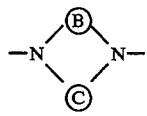

is the bis-bipyridine macrocycle (process C)

A - Sodium Cryptate of [bpy.bpy.(p-$OCH_3$-p-OH-diPhbpy)] (Compound 10)

A mixture of bis-bipyridine macrocycle (0.48 g, 1.21 mmol) and $Na_2CO_3$ (1.16 g, 11 mmol) in 480 ml of anhydrous $CH_3CN$ is refluxed for 30 min under nitrogen. A suspension of previously prepared 6,6'-dibromomethyl-4-p-methoxyphenyl-4'-p-hydro phenyl-2,2-bipyridine (see Example 1, section D) (0.65 g, 1.20 mmol) in 340 ml of $CH_3CN$ is added. The resulting solution is refluxed for 24 h under nitrogen. After it has returned to room temperature, the reaction mixture is filtered and the solvent is evaporated off. The crude product is then chromatographed on an alumina column with $CH_2Cl_2/CH_3OH$ (98/2) as the eluent.

Yield: 45%
TLC: $R_f=0.4$ (alumina, $CH_2Cl_2/CH_3OH$, 90/10) violet spot (254 nm), green spot (366 nm)
MS: a) IC ($NH_3$): 795 ($M^+$), 773 ($MH^+$-Na) b) $FAB^+$ (thioglycerol): 875 ($MBr^+$), 795 ($M^+$).

The sodium cryptate obtained was converted to the terbium cryptate by following the procedure described in Example 1H. This cryptate has the spectroscopic characteristics given below:
UV/visible in $H_2O$: 244 nm (maximum); 303 nm (maximum)
UV/visible in $CH_3OH$: 244 nm (maximum); 301 nm (maximum); 318 nm (shoulder).

B - Sodium Cryptate of [bpy.bpy.(p-$OCH_3$-p-$OCH_2CN$-diPhbpy)]

A solution of NaOH in $CH_3OH$ (1.5 equivalents in 2 ml) is added to a solution of the sodium cryptate of 10 (0.21 g, 0.24 mmol) in 12 ml of $CH_2Cl_2$ and 12 ml of $CH_3OH$. The mixture is refluxed for 1 h 30 min under nitrogen. The solvent is then evaporated off after the mixture has returned to room temperature; the water formed during the reaction is removed by azeotropic distillation with toluene. The product obtained in this way is dried overnight using a vane pump. The bright orange compound obtained is dissolved in 35 ml of THF (the solution is turbid). As soon as bromoacetonitrile is added (30 µl, 1.8 equivalents), the solution becomes clear. The reaction is left to proceed overnight at room temperature under nitrogen, with stirring. 20 ml of $H_2O$ and about 10 ml of $CH_2Cl_2$ are added. The medium is neutralized with a saturated solution of $NaHCO_3$. The organic phase is separated off and the aqueous phase is extracted twice with 20 ml of $CH_2Cl_2$. The resulting organic phase is dried over $Na_2SO_4$ and the solvents are then evaporated off. The crude product is chromatographed on an alumina column with $CH_2Cl_2/CH_3OH$ (95/5) as the eluent.

Yield: 92%
MS: $FAB^+$: 834 ($M^+$).

The sodium cryptate obtained was converted to the corresponding terbium cryptate by the procedure described in Example 1. This cryptate has the spectroscopic characteristics given below:

UV/visible in $CH_{30}H$: 300 nm (maximum); 314 nm (shoulder).

C - Rare Earth Cryptate of [bpy.bpy.(p-$OCH_3$-p-$OCH_2CH_2NH_2$-diPhbpy)]

The rare earth cryptate of the above compound is obtained by following the procedure described in section G of Example 1.

EXAMPLE 3

Preparation of the Europium Cryptate of [(bis-bpy)-bpy-di(Aamidoethyleneamine)] (Process A)

Compound of formula I: $Z=NH_2$; $Y=-CH_2-CH_2-$;

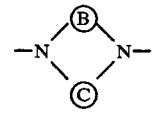

is the bipyridine macrocycle; R' is hydrogen

A - Preparation of the Sodium Cryptate of [(bis-bpy)-bpy-diester] (Compound of Formula 1 in which $R_1=CH_3$)

A mixture of 0.300 g (7.61·$10^{-4}$ mol) of the bis bipyridine macrocycle and 1.10 g (10.4·$10^{-3}$ mol) of $Na_2CO_3$ is refluxed for 30 min in 450 ml of $CH_3CN$. A solution of 0.350 g (7.64·$10^{-4}$ mol) of 6,6'-dibromomethyl-4,4'-p-dimethoxycarbonyl-2,2'-bipyridine (compound 1; X=Br) in 375 ml of $CH_3CN$ is then added over a period of 60 min, with vigorous stirring. The reaction mixture is stirred for a further 18 hours under reflux and then cooled to room temperature and filtered. The solvent is removed in vacuo on a rotary evaporator. The solid obtained is dissolved in CHCl₃ and chromatographed on an alumina column (with a small amount of silica at the top) by elution with CHCl₃/CH₃OH (98/2). The solvents are removed in vacuo and 0.230 g (38%) of the expected complex is obtained. This has the physicochemical characteristics given below:

Melting point >240° C.

¹H NMR (CD₃OD): 3.89 (s, 8H, CH₂-bpy); 3.98 (s, 4H, CH₂-bpy-diE); 4.03 (s, 6H, COOCH₃); 7.42 (d, J=7.4 Hz, 4H-bpy); 7.92 (t, J=7.4 Hz, 4H-bpy); 7.96 (d, J=1.2 Hz, 2H-bpy-diE); 8.10 (d, J=7.4 Hz, 4H-bpy); 8.60 (d, J=1.2 Hz, 2H-bpy-diE) (diE=diester)

¹³C NMR (CDCl₃): 52.9, 59.5, 119.7, 120.4, 123.4, 124.1, 138.2, 139.7, 155.2, 155.7, 158.3, 160.4, 164.9

$C_{40}H_{34}N_8O_4NaBr.4H_2O$ (865.71): Calculated (%): C 55.49; H 4.89; N 12.94 Found (%): C 55.44; H 4.33; N 13.10

B - Aminolysis of the above Cryptate

The cryptate obtained above (0.100 g, $1.26 \cdot 10^{-4}$ mol) is subjected to aminolysis by being added in portions to 4 ml of ethylenediamine distilled over KOH and heated to 90° C. beforehand. The reaction mixture obtained is stirred for a further 1 hour and then cooled to room temperature. The excess ethylenediamine is then removed in vacuo to give an oil. This is taken up in 2 ml of a CHCl₃/CH₃OH mixture (2/1), which is in turn removed in vacuo. Purification is repeated 5 times to give the expected complex with a yield of 89%.

C - Conversion of the above Cryptate to the Corresponding Europium Cryptate

The europium cryptate of [(bis-bpy)(bpy-di(amidoethyleneamine))] was obtained by following the procedure described in section H of Example 1; it has the spectroscopic characteristics given below:

UV/visible in H2O 240 nm; 303 nm (maxima)

EXAMPLE 4

Preparation of the Europium Cryptate of [(bis-bpy)(bpy-di(Amidoethyleneamine))] (Process A)

Compound of formula I: Z=NH₂; Y=—CH₂—CH₂—; R'=H;

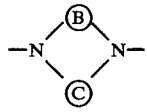

is the bipyridine macrocycle

A - Preparation of the Europium Cryptate of [(bis-bpy)-(bpy-diester)]

The sodium cryptate obtained in section A of the previous example (0.10 mmol) is dissolved in 8 ml of CHCl₃ and added to a solution of EuCl₃.6H₂O (0.15 mmol) in 40 ml of CH₃OH. The solution is stirred at the reflux temperature, under nitrogen, until the sodium cryptate disappears (TLC, aluminum oxide, eluent: CH₂Cl₂/CH₃OH (90/10)). The reaction time is of the order of 48 hours. The reaction mixture is cooled to room temperature and filtered if turbidity is present. The solvents are removed on a rotary evaporator and the residue is redissolved in 20–25 ml of CH₃OH. Ethyl ether is added dropwise until a very slight turbidity persists. The europium cryptate crystallizes in this way at room temperature. The solvents are removed with a pipette and the cryptate is dried. Yield: about 40% (first crystallization). The filtrate is concentrated to dryness and the operation is repeated.

The product obtained has the physicochemical characteristics given below:

1. ¹H NMR (D₂O, ref. =t-BuOH): 10.51 (2H, s, CH(bpy-diE)); 8.66 (2H, s, CH-bpy-diE); 8.06 (4H, t, CH-bpy); 7.08 (4H, d, CH-bpy); 6.74 (4H, d, CH-bpy); 4.66 (6H, s, OCH₃); 0.9 (8H, s, CH₂-bpy); −0.78 (4H, s, CH₂-bpy-diE)

$C_{40}H_{34}N_8O_4\text{-EuCl}_3.NaCl.9/2H_2O$ (1088.58) Calculated %: C 44.13; H 3.98; N 10.29 Found %: C 43.93; H 3.79; N 9.88 C 44.06; H 3.70; N 10.03

B - Aminolysis of the Europium Cryptate

The europium cryptate obtained above (40 mg) is added in portions to 40 ml of ethylenediamine distilled over KOH beforehand. The clear solution is stirred for 3 hours at room temperature, under nitrogen. The ethylenediamine is removed in vacuo on a rotary evaporator. The residue is taken up in a few milliliters of CH₂Cl₂/MeOH (2/1) and the solvents are removed in vacuo. The operation is repeated 5 times to give a perfectly solid compound. The cryptate obtained is dried for 24 hours under a vane pump vacuum.

Melting point=168°–170° C.

This europium cryptate has the same characteristics as the europium cryptate obtained in the previous example. These two examples therefore show that it is possible to carry out complexation of the alkali metal cryptate with a rare earth ion before or after substitution.

EXAMPLE 5

Preparation of the Europium or Terbium Cryptate of [(22)bpy-di(Amidoethyleneamine)]

Compound of formula I:

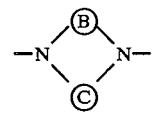

is the macrocycle (22); Z=NH₂; Y=—CH₂—CH₂—

A - Preparation of the Sodium Cryptate of [(22)bpy-diester]

A mixture of 0.114 g ($4.37 \cdot 10^{-4}$ mol) of the macrocycle (22) and 0.460 g ($4.34 \cdot 10^{-3}$ mol) of Na₂CO₃ is refluxed for 30 min in 130 ml of CH₃CN. A solution of 0.200 g ($4.37 \cdot 10^{-4}$ mol) of the compound 1 in 220 ml of CH₃CN is then added over a period of 60 min, with vigorous stirring. The reaction mixture is stirred for a further 15 hours under reflux and then cooled to room temperature and filtered. The solvent is removed in vacuo on a rotary evaporator. The solid obtained is dissolved in CH₂Cl₂ and purified by chromatography on an alumina column (with a small amount of silica at the top). An impurity is first eluted with CH₂Cl₂. The macrobicycle formed is then eluted with CH₂Cl₂/CH₃OH (98/2). The solvents are removed in vacuo and 0.135 g (61%) of the macrobicycle is obtained.

B - Preparation of the Europium or Terbium Cryptate of [(22)bpy-diester]

The europium and terbium cryptates of [(22)bpy-diester] were obtained by following the procedure described in Example 1H; they have the spectroscopic characteristics given below:

europium cryptate: UV/visible in CH₃OH 242 nm and 324 nm (maxima)

terbium cryptate: UV/visible in CH3OH 242 nm and 325 nm (maxima)

C - Preparation of the Europium Cryptate of [(22)bpy-di(amidoethyleneamine)]

The europium cryptate obtained above (0.100 g, 1.43·10⁻⁴ mol) is added in portions to 5 ml of ethylenediamine distilled over KOH and heated to 90° C. beforehand. The reaction mixture is stirred for a further 1 hour and then cooled to room temperature. The excess ethylenediamine is removed in vacuo to give an oil. This is taken up in 2 ml of CHCl3, which is in turn removed in vacuo. Purification is repeated 3 times and 93 mg (90%) of the europium cryptate are obtained. This cryptate has the spectroscopic characteristics given below:

UV/visible in H2O 240 and 315 nm (maxima)

The terbium cryptate obtained in section B can be subjected to aminolysis in the same way.

EXAMPLE 6

Preparation of the Sodium Cryptate of [(bpy-Dicarbomethoxy)3] (Process B)

Formula 7: R'=R''=OCH3;

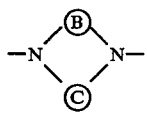

is the bis-bipyridine macrocycle

A - Synthesis of 4,4'-dicarbomethoxy-6,6'-diazidomethyl-2,2'-bipyridine

A mixture of 4,4'-dicarbomethoxy-6,6'-dibromomethyl-2,2'-bipyridine (0.50 g, 1.10·10⁻³ mol) and NaN3 (1.0 g, 15.4·10⁻³ tool) is refluxed for 36 hours in 15 ml of THF. The reaction mixture is cooled to room temperature, filtered over celite and concentrated to dryness. The residue is dissolved in CHCl3 and chromatographed on a silica column by elution with CHCl3.

Evaporation of the solvent gives 0.40 g (95%) of the expected compound, which has the physicochemical characteristics given below:

M.p.=168°-170° C.

$^1$H NMR (CDCl3): 4.02 (s, 6H, COOCH3); 4.63 (s, 4H, CH2—H3); 7.94 (d, J=1.3 Hz, 2H); 8.96 (d, J=1.3 Hz, 2H)

$^{13}$C NMR (CDCl3): 52.7; 55.1; 120.0; 121.5; 139.7; 156.0; 156.8; 165.3.

IR (KBr): 1715 cm⁻¹ (ester), 2090 cm⁻¹ (azide)

MS: 383 ((MH)+)

C6H14N8O4 (382.34) Calculated %: C 50.27; H 3.69; N 29.31 Found %: C 50.37; H 3.51; N 27.69

B - Synthesis of 4,4'-dicarbomethoxy-6,6'-diaminomethyl-2,2'-bipyridine (Compound 5)

A mixture of the compound obtained according to A (0.126 g, 3.30·10⁻⁴ mol) and 12.6 mg of 10% Pd/C in 38 ml of CH2Cl2/CH3OH (2/1) is stirred at room temperature under a hydrogen atmosphere for 12 hours.

The reaction mixture is filtered over celite and evaporation of the solvents gives 0.100 g (92%) of the expected compound, which is used without purification in the next step.

C - Synthesis of the Sodium Cryptate of [bpy-dicarbomethoxy]3 Compound 7)

A mixture of 6 (R'=OCH3; X=Br) (0.280 g, 6.11·10⁻⁴ mol) and Na2CO3 (0.65 g, 6.13·10⁻³ mol) is heated to the reflux temperature in 500 ml of CH3CN. 0.100 g (3.03·10⁻⁴ mol) of 5 is then added and the reaction mixture is stirred under reflux for a further 48 hours. It is cooled to room temperature and filtered. The solvent is removed in vacuo. The residue is taken up in CHCl3 and chromatographed on an alumina column (with a small amount of silica at the top) by eluting with CHCl3/MeOH (98/2). Evaporation of the solvents gives 0.132 g (40%) of the macrobicycle 7 (R''=R'=OCH3).

M.p.>250° C.

$^1$H NMR (CDCl3): 4.02 (s, 18H, COOCH3); 4.08 (s, 12H, CH2); 7.96 (d, J=1.2 Hz, 6H); 8.49 (d, J=1.2 Hz, 6H)

$^{13}$C NMR (CDCl3): 53.2; 59.2; 120.0; 123.8; 139.9; 155.6; 159.9; 164.8.

C48H42N8O12·NaBr·3H2O (1079.84) Calculated %: C 53.39; H 4.48; N 10.38 Found %: C 53.40; H 4.40; N 9.75

The cryptate obtained above can be subjected to aminolysis with ethylenediamine by the procedure described in the previous examples. This generally gives a mixture of cryptates which are monosubstituted or disubstituted to hexasubstituted by the group CO—NH—CH2—CH2—NH2; these compounds can be separated by conventional means.

EXAMPLE 7

Preparation of the Europium Cryptate of [bis(bpy-Dicarboxybutoxy)-bpy-Diamidoethyleneamine]

Formula I: Y=—CH2—CH2—; Z=NH2;

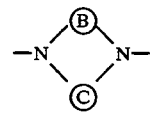

is the bis-bipyridine macrocycle; R'=t-Bu (tert.-butyl or Bu$^t$)

A - Preparation of the Sodium Cryptate of [bis(bpy-dicarboxybutoxy)-bpy-dicarboxymethoxy]

The sodium cryptate of formula 7 (R'=COO(t-C4H9); R''=COOCH3) was obtained by following the procedure described in Example 6 and using the compound 5 obtained in section B of this example and the compound 6 (R'=COO(t-C4H9); X=Br); the said cryptate has the physicochemical characteristics given below:

M.p.>220° C.

$^1$H NMR (CDCl3): 1.60 (s, 36H, COOBu$^t$); 3.99; 4.02; 4.06 (3s, 18H, CH2-bpy-diCOOMe+CH2-bpy-diCOOBu$^t$+—COOCH3); 7.81 (s, 4H, bpy-diCOOBu$^t$); 7.95 (s, 2H, bpy-diCOOMe); 8.36 (s, 4H, bpy-diCOOBu$^t$); 8.45 (s, 2H, bpy-diCOOMe)

$^{13}$C NMR (CDCl3): 28.0; 53.1; 59.1; 83.4; 119.8; 119.9; 123.4; 123.7; 139.8; 141.7.

C60H66N8O12·NaBr·3H2O (1248.18) Calculated %: C 57.73; H 5.81; N 8.98 Found %: C 57.99; H 5.31; N 9.03

This sodium cryptate was then converted to the corresponding europium cryptate by the procedure described above.

The europium cryptate was then subjected to aminolysis with ethylenediamine.

In a variant, it is possible firstly to subject the above compound 7 to aminolysis and then to convert the sodium cryptate obtained to the corresponding europium cryptate by following the procedures described above.

APPLICATION OF THE COMPOUNDS AS FLUORESCENT TRACERS

As indicated above, the compounds of the invention are suitable as agents for labeling biological substances, this being carried out by coupling the compound of the invention by covalent bonding with the biological substance to be assayed or detected. This coupling can be effected by the conventional coupling processes used in this field, for example the SMCC/SPDP or carbodiimide processes.

The cryptates according to the invention are suitable as fluorescent tracers in all types of process for the determination or detection of biological substances, and especially in the so-called methods of assay by competition or in the so-called methods of assay by excess, in the homogeneous phase or in the heterogeneous phase, the said processes being well known to those skilled in the art and described in particular by LANDON, Ann. Clin. Biochem. 1981, 18, p. 253, and SOINI, Clin. Chemi. 25, 353, 1979. The cryptates can also be used in the homogeneous process of detection and/or determination by luminescence which is described in International Application WO 87/00927.

The biological substances to be detected or determined can be, for example, antibodies, antigens, toxins, enzymes, proteins, hormones, hormone receptors, steroids, avidin, biotin, microorganisms, haptens, nucleic acids, DNA and RNA fragments, lipids, carbohydrates, etc. Examples of such substances are cited in the description of European Patent Application 17 908, which is incorporated in the present description by way of reference.

The use of the compounds of the invention as fluorescent tracers is illustrated by the following three experiments:

In experiment A below, the reagents SPDP and sulfo-SMCC were used, these being respectively: "N-succinimidyl 3-(pyridyl-2-thio)propionate" and "sulfosuccinimidyl 4-(N - maleimidomethyl)cyclohexane-1carboxylate".

EXPERIMENT A

Formation of an Antibody-cryptate Conjugate Using SMCC/SPDP

1) Activation of the Europium Cryptate Obtained According to Example 3

50 $\mu$l of a solution of sulfo-SMCC containing 13.1 mg/ml in a 20 mM phosphate buffer of pH 7 are added to 500 $\mu$l of a solution of the above cryptate containing 1.5 mg/ml in the same buffer.

The mixture is then incubated for 30 min at room temperature and shaken on a Vortex for 5 min. The solution is centrifuged to remove the precipitate. Purification is carried out by passage over a Pharmacia Mono Q ion exchange column, forming a gradient between:

Buffer A: 20 mM phosphate of pH 7+10% of DMF
Buffer B: 20 mM phosphate of pH 7+10% of DMF+1 mol/l of NaCl The cryptate is detected by measuring its absorption at 307 nm ($\epsilon$=25000 M$^{-1}$cm$^{-1}$ at 307 nm).

The activated cryptate comes out in the dead volume. The excess sulfo-SMCC is eluted in the gradient.

2) Activation of the Antibody

The E$_1$ monoclonal antibody used is the antiprolactin antibody contained in the prolactin radioimmunoassay kits manufactured by the company ORIS INDUSTRIE and known under the name "ELSA PROL".

30 $\mu$l of a 30 mM solution of SPDP in absolute ethanol are added to 1.2 ml of a solution of E$_1$ antibody containing 14.8 mg/ml in a 50 mM phosphate buffer containing 150 mmol/l of NaCl, of pH 7.1.

The mixture is incubated for 30 min at room temperature, with shaking.

The solution is passed over a column of Pharmacia G25 gel equilibrated with the same phosphate buffer ($\epsilon$=210,000 M$^{-1}$cm$^{-1}$ at 280 nm).

The fraction eluted in the dead volume is recovered.

60 $\mu$l of a 400 mM solution of DTT (dithiothreitol) in phosphate buffer are added.

The mixture is incubated for 15 min at room temperature, with shaking, and the fraction which comes out in the dead volume after passage over a G25 column equilibrated in phosphate buffer is recovered.

3) Coupling of the Activated Antibody with the Activated Cryptate

50 $\mu$l of a solution of cryptate containing 200 $\mu$mol/l are added to 60 $\mu$l of a solution of activated antibody containing 2.6 mg/ml in a phosphate buffer.

The mixture is incubated for 12 hours at room temperature and centrifuged. The supernatant is dialyzed against a 50 mM phosphate buffer of pH 7.4.

EXPERIMENT B

Formation of an Antibody-cryptate Conjugate Using Carbodiimide

1) Succinylation of the Antibody

83 $\mu$l of a solution containing 50 mg/ml of succinic anhydride in DMSO ($\frac{1}{3}$)/100 mM borate of pH 9 ($\frac{2}{3}$) are added in three portions to 440 $\mu$l of a solution of E$_1$ antibody containing 9.4 mg/ml in 100 mM borate of pH 9, immersed in melting ice.

The pH is kept at 9 with sodium hydroxide. The reaction is allowed to proceed for 30 min at 0° C.

2) Purification

This is carried out by high pressure chromatography on a column of TSK 3000 SW filtration gel, the eluent being a 50 mM phosphate buffer of pH 7.4. Flow rate: 1 ml/min.

The succinylated antibody is recovered in a volume of 3 ml, which is concentrated to 370 $\mu$l.

3) Coupling of the Succinylated Antibody with the Cryptate

Solution 1: 25.5 mg of carbodiimide are mixed with 1335 $\mu$l of 50 mM phosphate buffer of pH 7.4

Solution 2: 50 mg/ml of sulfo-N-hydroxysuccinimide in the same buffer (14.7 mg in 222.7 $\mu$l)

Solution 3: 0.96 mg/ml of cryptate according to Example 3 in the same buffer.

The following are reacted for 1 hour at room temperature:

175 $\mu$l of solution of succinylated antibody
480 $\mu$l of solution 3
72.5 $\mu$l of solution 1
10 $\mu$l of solution 2

After exhaustive dialysis against 50 mM phosphate buffer of pH 7.4, the product is concentrated on an Amicon cone to give a conjugate solution containing 0.86 mg/ml.

The product is frozen in buffer with 1 mg/ml of human serum albumin (HSA).

RESULTS: PROLACTIN ASSAY

The reagents used are taken from the ELSA-PROL prolactin assay kit.

The following are added to each tube containing the ELSA solid phase:

100 μl of standard

300 μl of $E_1$-cryptate conjugate obtained according to experiments A or B in 50 mM phosphate buffer of pH 7.4 with 1 mg/ml of HSA.

The mixture is incubated for 3 hours at 37° C.

The solid phase is left with 2 times 3 ml of $H_2O$.

400 μl of buffer containing 5 mmol/l of sodium dodecyl-sulfate (SDS) are added.

300 μl of this solution are transferred to an ARCUS LKB instrument for measurement of the fluorescence.

The results obtained are plotted on the attached FIG. 1. On this figure, the intensity of the fluorescence has been plotted on the ordinate and the amount of prolactin in μU/ml on the abscissa.

These results show that the cryptates according to the invention are suitable as fluorescent tracers in an immunoassay.

Experiment C below illustrates the use of the cryptates according to the invention in the homogeneous process according to International Application WO 87/00927.

EXPERIMENT C

Prolactin Assay

I - Homogeneous Prolactin Assay

A - Fixing of Iodine to the Antibody

The $G_2$ anti-prolactin monoclonal antibody is labeled with Wood's reagent [described in synthesis, Anal. Biochem. 69, 339–349 (1975)].

2.93 mg of Wood's reagent are dissolved in 40 μl of 0.5N sodium hydroxide.

400 μl of 200 mM carbonate buffer of pH 9.3 are added.

200 μl of a solution of $G_2$ antibody containing 10 mg/ml in a 100 mM carbonate buffer of pH 9.3 are added to the above solution and the mixture is incubated for 17 hours at 30° C.

It is purified on a Pharmacia PD10 column with a 100 mM carbonate buffer of pH 9.3.

The fractions eluted in the dead volume are collected; the conjugate is characterized by the ratio of its optical densities at 320 and 280 nm:

$$\frac{OD\ 320}{OD\ 280} \simeq 1.4\ \text{to}\ 1.5$$

Its concentration is estimated by assuming that 90% of the antibodies are recovered. The conjugate is divided up into aliquots and stored at −20° C.

B - Prolactin Assay (curve A)

Prolactin standards containing 0, 15, 30, 60 and 150 ng/ml are used. The assay is performed in EFLAB 12-well blocks, catalog no. 96 02 107.

The following are added in succession:

100 μl of standard

100 μl of solution of Wood's $G_2$ antibody containing 5 μg/ml

100 μl of solution of $E_1$ conjugate from experiment A, containing 0.375 μg/ml

The mixture is incubated for 15 minutes at room temperature.

It is measured on the ARCUS instrument.

Figure 2:
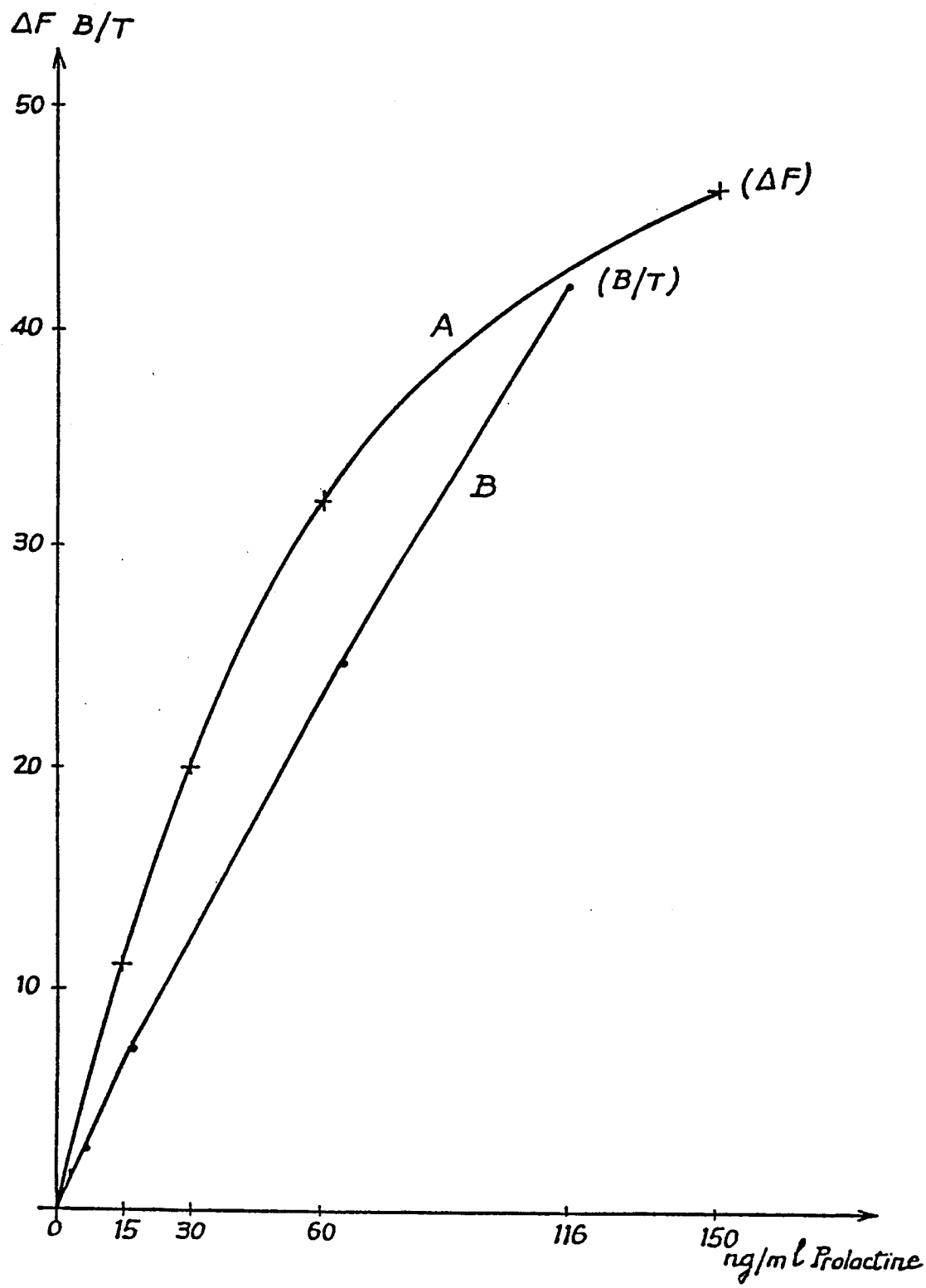
FIG. 2 is a graph plotting (1) in Curve A, the value ΔF versus the value of standards (prolactin standards containing 0, 15, 30, 60 and 150 ng/ml were used), where ΔF=(fluorescence of a standard minus fluorescence of standard 0)/fluorescence of standard ); (2) in Curve B, the value B/T versus the value of the standards, where B is the radioactivity counted for the standard and T is the radioactivity counted for 300 μl of the radioactive tracer.

A standard curve is drawn by plotting the value ΔF against the value of the standards (FIG. 2), where ΔF = fluorescence of the standard measured −

$$\frac{\text{fluorescence of standard 0}}{\text{fluorescence of standard 0}}$$

I - Prolactin Radioimmunoassay (curve B)

The ELSA-PRL kit (ORIS company) is used.

The following are added to the ELSA tube:

300 μl of the radioactive tracer

100 μl of standard

After shaking, the mixture is incubated for 3 hours at 37° C.

The tubes are washed twice with water.

The tubes are counted on a counter.

The value B/T is plotted for each standard (FIG. 2), where

B=radioactivity counted for the standard

T=radioactivity counted for 300 μl of the radioactive tracer.

The results obtained (see FIG. 2) show that the cryptates according to the invention are suitable as tracers in the homogeneous process according to International Application WO 87/00927. Furthermore, it may be noted that, by virtue of the cryptates according to the invention, this homogeneous process is particularly advantageous by comparison with the assay process using a radioactive element, which requires a much longer incubation time, washing steps and the handling of radioactive elements.

What is claimed is:

1. A method of labeling a biological substance comprising coupling said substance with a rare earth cryptate consisting essentially of at least one rare earth salt complexed by a macropolycyclic compound of formula I or II:

in which:

(a) the ring of the formula

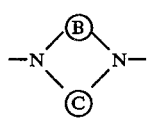

is a macrocycle of the formula:

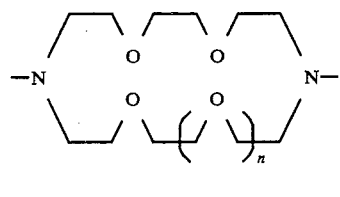

or

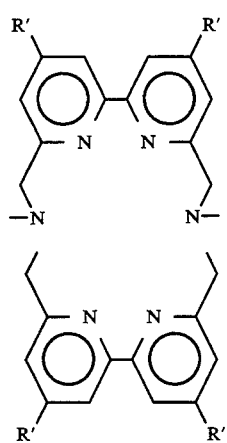

where n=0 or 1,
where R' is hydrogen, —CO—N—H—Y—Z, or —COOR' in which R' is C$_1$-C$_{10}$ alkyl;

(b) Y is a divalent organic radical selected from the group consisting of (1) linear or branched C$_1$-C$_{20}$ alkylene group optionally containing at least one double bond and optionally being interrupted by one or more heteroatoms selected from the group consisting of O, N, S and P, (2) C$_5$-C$_8$ cycloalkylene group optionally substituted by an alkyl, aryl or sulfonate group; and (3) C$_6$-C$_{14}$ arylene group optionally substituted by an alkyl, aryl or sulfonate group;

(c) Z is a functional group capable of bonding covalently with said biological substance; and (d) R is methyl or the group —Y—Z where Y and Z are as defined above.

2. The method of claim 1 in which the macropolycyclic compound is of Formula I.

3. The method of claim 1 in which the macropolycyclic compound is of Formula II.

4. The method of claim 1 in which

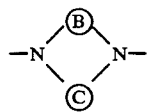

is the bis-bipyridine molecule.

5. The method of claim 1 in which

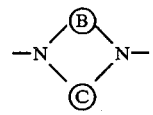

is selected from the group consisting of [N$_2$O$_4$] and [N$_2$O$_3$].

6. The method of claim 1 in which Y is selected from the group consisting of —CH$_2$— and —CH$_2$CH$_2$—.

7. The method of claim 1 in which Z is selected from the group consisting of NH$_2$ and CN.

8. The method of claim 1 in which R is CH$_3$.

9. The method of claim 15 in which R' is H.

10. A method of detecting or determining a biological substance in a sample comprising coupling said biological substance with a rare earth cryptate consisting essentially of at least one rare earth salt complexed by a macropolycyclic compound of formula I or II:

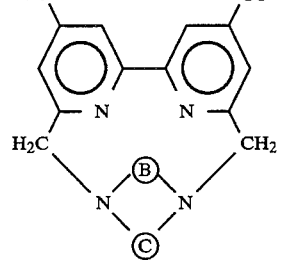

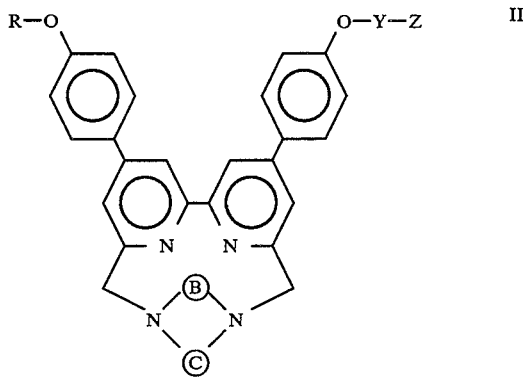

in which:
(a) the ring of the formula

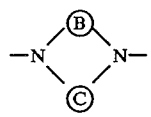

is a macrocycle of the formula:

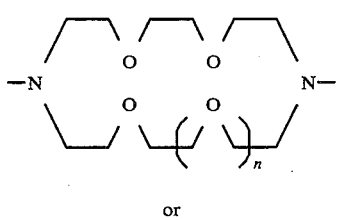

or

-continued

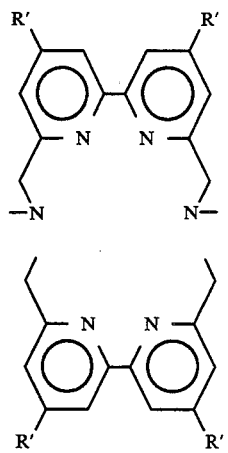

where n=0 or 1, where R' is hydrogen, —CO—N—H—Y—Z, or —COOR' in which R' is $C_1$–$C_{10}$ alkyl;

(b) Y is a divalent organic radical selected from the group consisting of (1) linear or branched $C_1$–$C_{20}$ alkylene group optionally containing at least one double bond and optionally being interrupted by one or more heteroatoms selected from the group consisting of O, N, S and P, (2) $C_5$–$C_8$ cycloalkylene group optionally substituted by an alkyl, aryl or sulfonate group; and (3) $C_6$–$C_{14}$ arylene group optionally substituted by an alkyl, aryl or sulfonate group;

(c) Z is a functional group capable of bonding covalently with said biological substance; and (d) R is methyl or the group —Y—Z where Y and Z are as defined above;

and detecting or determining the fluorescence of said sample.

11. A method for detecting or determining a biological substance in a sample comprising coupling said biological substance with a rare earth cryptate consisting essentially of at least one rare earth salt complexed by a macropolycyclic compound of formula I or II:

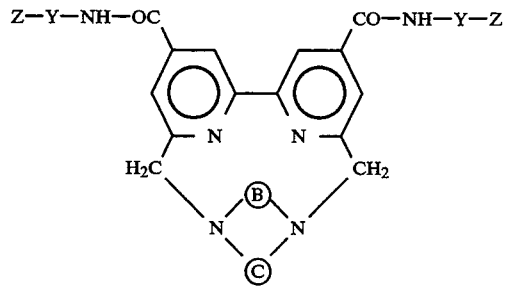

-continued

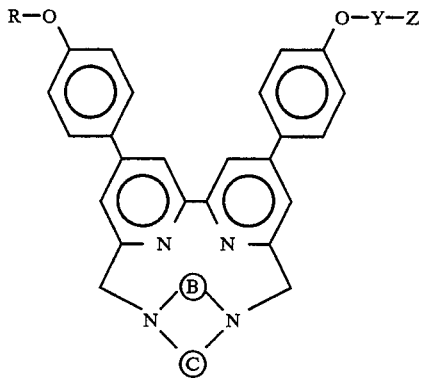

in which:
(a) the ring of the formula

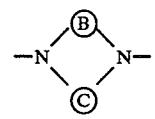

is a macrocycle of the formula:

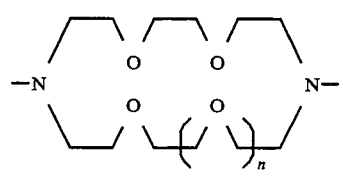

or

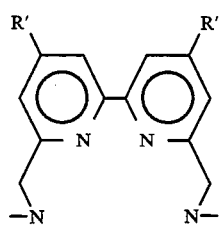

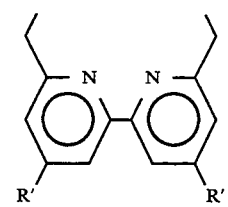

where n=0 or 1,
where R' is hydrogen, —CO—NH—Y—Z, or —COOR' in which R' is $C_1$–$C_{10}$ alkyl;

(b) Y is a divalent organic radical selected from the group consisting of (1) linear or branched $C_1$–$C_{20}$ alkylene group optionally containing at least one double bond and optionally being interrupted by one or more heteroatoms selected from the group consisting of O, N, S and P, (2) $C_5$–$C_8$ cycloalkylene group optionally substituted by an alkyl, aryl or sulfonate group; and (3) $C_6$–$C_{14}$ arylene group optionally substituted by an alkyl, aryl or sulfonate group;

(c) Z is a functional group capable of bonding covalently with said biological substance; and (d) R is methyl or the group —Y—Z where Y and Z are as defined above;

and detecting or determining the luminescence of said sample.

* * * * *

UNITED STATES PATENT AND TRADEMARK OFFICE
CERTIFICATE OF CORRECTION

PATENT NO. : 5,346,996
DATED : September 13, 1994
INVENTOR(S) : Jean-Marie Lehn, Gérard Mathis, Béatrice Alpha, Robert Deschenaux and Etienne Jolu It is certified that error appears in the above-indentified patent and that said Letters Patent is hereby corrected as shown below:

Column 7, line 25 under the drawing, delete "7" and insert --- 8 --- therefor.

Column 24, line 15, delete "claim 15" and insert --- claim 1 --- therefor.

Signed and Sealed this

Twenty-fourth Day of October, 1995

Attest:

BRUCE LEHMAN

*Attesting Officer*      *Commissioner of Patents and Trademarks*